US006418227B1

(12) United States Patent
Kuo

(10) Patent No.: US 6,418,227 B1
(45) **Date of Patent: *Jul. 9, 2002**

(54) ACTIVE NOISE CONTROL SYSTEM AND METHOD FOR ON-LINE FEEDBACK PATH MODELING

(75) Inventor: Sen M. Kuo, DeKalb, IL (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/991,726

(22) Filed: Dec. 16, 1997

Related U.S. Application Data

(60) Provisional application No. 60/033,458, filed on Dec. 17, 1996, provisional application No. 60/033,107, filed on Dec. 17, 1996, provisional application No. 60/033,106, filed on Dec. 17, 1996, provisional application No. 60/033,105, filed on Dec. 17, 1996, and provisional application No. 60/033,104, filed on Dec. 17, 1996.

(51) Int. Cl.[7] .................................................. A61F 11/06
(52) U.S. Cl. .................. 381/71.11; 381/71.1; 381/71.5
(58) Field of Search .............................. 381/71.1, 71.5, 381/71.11

(56) References Cited

U.S. PATENT DOCUMENTS 4,677,676 A * 6/1987 Eriksson .................... 381/71.1
4,677,677 A * 6/1987 Eriksson .................... 381/71.1
5,018,202 A * 5/1991 Takahashi et al. ......... 381/71.1
5,499,302 A * 3/1996 Nagami et al. ............... 381/71
5,745,580 A * 4/1998 Southward et al. ........ 381/71.1
5,852,667 A * 12/1998 Pan et al. .................. 381/71.1
5,940,519 A * 8/1999 Kuo .......................... 381/71.1
5,945,019 A * 8/1999 Kuo .......................... 381/71.1
5,991,418 A * 11/1999 Kuo .......................... 381/71.1
6,097,823 A * 8/2000 Kuo .......................... 381/71.1

* cited by examiner

*Primary Examiner*—Forester W. Isen
*Assistant Examiner*—Laura A. Grier
(74) *Attorney, Agent, or Firm*—Robert D. Marshall, Jr.; W. James Brady, III; Frederick J. Telecky, Jr.

(57) ABSTRACT

A feedforward active noise control system (50) is provided for generating an anti-noise signal to attenuate a noise signal provided through a media. The feedforward active noise control system (50) performs on-line feedback path modeling and feedback path neutralization and includes a reference sensor (16), a secondary source (18), an error sensor (20), and an active noise control system controller (10). The reference sensor (16) receives the noise signal and a feedback signal (22) and generates a primary signal x(n). The secondary source (18) receives a secondary signal s(n) and generates a corresponding anti-noise signal. The error sensor (20) receives a residual signal and generates an error signal e(n) in response. The active noise control system controller (10) receives the primary signal x(n) and the error signal e(n) and generates the secondary signal y(n) while performing on-line feedback path modeling.

33 Claims, 2 Drawing Sheets

ACTIVE NOISE CONTROL SYSTEM AND METHOD FOR ON-LINE FEEDBACK PATH MODELING

RELATED APPLICATIONS

This application claims priority under 35 USC 119(e) (1) of provisional application No. 60/033,106, filed Dec. 17, 1996.

This application is related to the following U.S. Provisional Applications all filed concurrently on Dec. 17, 1996:

- Provisional Application No. 60/033,458, from which U.S. patent application Ser. No. 08/992,823 entitled Active Noise Control System and Method for On-Line Feedback Path Modeling and On-Line Secondary Path Modeling, now U.S. Pat. No. 5,940,519, claims priority;
- Provisional Application No. 60/033,104, from which U.S. patent application Ser. No. 08/992,699 entitled Off-Line Feedback Path Modeling Circuitry and Method for Off-Line Feedback Path Modeling, now U.S. Pat. No. 6,198,828, claims priority;
- Provisional Application No. 60/033,107, from which U.S. patent application Ser. No. 08/992,933 entitled Off-Line Path Modeling Circuitry and Method for Off-Line Feedback Path Modeling and Off-Line Secondary Path Modeling, now U.S. Pat. No. 5,991,418, claims priority; and
- Provisional Application No. 60/033,105, from which U.S. patent application Ser. No. 08/992,777 entitled Digital Hearing Aid and Method for Active Noise Reduction, now U.S. Pat. No. 6,097,823, claims priority.

TECHNICAL FIELD OF THE INVENTION

This invention relates generally to the field of control systems and more particularly to an active noise control system and method for on-line feedback path modeling.

BACKGROUND OF THE INVENTION

Active noise control systems are concerned with the reduction of any type of undesirable disturbance or noise signal provided by a noise source through an environment, whether it is borne by electrical, acoustic, vibration, or any other kind of noise media. Since the noise source and environment are often time-varying, the noise signal will often be non-stationary with respect to frequency content, amplitude, and velocity. Active noise control systems control noise by introducing a canceling "anti-noise" signal into the system environment or media through an appropriate secondary source. The anti-noise signal is ideally of equal amplitude and 180 degrees out of phase with the noise signal. Consequently, the combination of the anti-noise signal with the noise signal at an acoustical summing junction results in the cancellation or attenuation of both signals and hence a reduction in noise.

In order to produce a high degree of noise signal attenuation, the amplitude and phase of both the noise and anti-noise signals must match closely as described above. Generally, this is accomplished by an active noise control system using an active noise control system controller that performs digital signal processing using one or more adaptive algorithms for adaptive filtering. The adaptive filtering, and more specifically the adaptive algorithms, track all of the changes in the noise signal and the environment in real-time by minimizing an error signal and continuously tracking time variations of the environment. The adaptive filtering may use any of a variety of known and available adaptive algorithms, such as the least-mean-square ("LMS") algorithm, to establish the taps or coefficients of an associated adaptive filter that models the noise source and environment to reduce or minimize the error or residual signal.

Active noise control systems, as compared to passive noise control systems, provide potential benefits such as reduced size, weight, volume, and cost in addition to improvements in noise attenuation. Active noise control is an effective way to attenuate noise that is often difficult and expensive to control using passive means and has application to a wide variety of problems in manufacturing, industrial operations, and consumer products.

Active noise control systems may generally be divided into feedforward active noise control systems and feedback active noise control systems. The present invention will be illustrated as applied to a feedforward active noise control system and thus the present invention will be described in this context.

A feedforward active noise control system generally includes a reference sensor for sensing a noise signal from a noise source and generating a corresponding primary signal in response; an active noise control system controller for generating a secondary signal; a secondary source, located downstream from the reference sensor, for receiving the secondary signal and generating an anti-noise signal to cancel or attenuate the noise signal; and an error sensor for detecting a residual signal and generating a corresponding error signal in response. The residual signal is equivalent to the difference between the noise signal and the anti-noise signal as provided to the error signal through a primary environment. The active noise control system controller receives the primary signal and the error signal and generates the secondary signal in response.

The active noise control system controller is implemented using a digital signal processor and performs digital signal processing using a specific adaptive algorithm, depending on the type of cancellation scheme employed, for adaptive filtering. Also, the reference sensor, the secondary source, and the error sensor may include interface circuitry for interfacing with the active noise control system controller. The interface circuitry may include analog-to-digital converters, digital-to-analog converters, analog filters such as low pass filters and automatic gain control amplifiers so that signals can be exchanged in the correct domain, i.e., either the digital or analog domain. The interface circuitry may be provided separately.

Feedforward active noise control systems include a primary path that has a transfer function that may be denoted as P(z). The primary path may be defined as the environment from the reference sensor to the error sensor. Feedforward active noise control systems also include a secondary path and a feedback path. The secondary path has a transfer function that may be denoted as S(z). The secondary path may be defined as the environment from the output of the active noise control system controller to the output of the error sensor. This may include interface circuitry such as a digital-to-analog converter, an analog filter, a power amplifier, a loud speaker, an error microphone, and other devices. The feedback path also has a transfer function and may be denoted by F(z). The feedback path may be defined as the environment from the output of the active noise control system controller to the output of the reference sensor. The active noise control system controller, using a digital signal processor, may include an adaptive filter, that is normally denoted by W(z), that attempts to adaptively model the primary path. The objective of the adaptive filter W(z) is to minimize the residual signal or error signal. The adaptive filtering performed by adaptive filter W(z) may be performed either on-line or off-line.

Feedforward active noise control systems suffer from a serious drawback that often harms overall system performance. Whenever the secondary source generates an anti-noise signal to cancel the noise signal, a portion of the anti-noise signal radiates upstream to the reference sensor where it is received along with the noise signal. The path that the anti-noise signal takes when traveling from the secondary source to the reference sensor is the feedback path. The feedback path, once again, may be defined as the media environment from the output of the active noise control system controller to the output of the reference sensor. The portion of the anti-noise signal flowing to the reference sensor along the feedback path is part of a feedback signal that travels through the feedback path. As a consequence of the feedback signal being received at the reference sensor, an incorrect primary signal is provided to the active noise control system controller by the reference sensor and, hence, overall system performance is harmed. If the feedback signal is in phase with the noise signal, the reference sensor will generate a primary signal that is too large. If the feedback signal is out of phase with the noise signal, the reference senor will also generate a signal that is incorrect. In any event, the feedback signal is undesirable and harms overall performance. The feedback signal may also allow the introduction of poles into the response of the system transfer function which results in potential instability if the gain of the feedback loop becomes large.

In certain applications, overall system performance is significantly degraded if the effects of the feedback path are not modeled and neutralized. The modeling of the feedback path and neutralization of the feedback signal becomes especially critical to overall active noise control system performance in applications in which the secondary source is in close proximity or in close communication with the reference sensor. Such systems would include, for example, appliances such as refrigerators and window air conditioner units in which the air ducts are relatively short. In such applications, the secondary source must be located close to the reference sensor by necessity and hence the feedback signal and its adverse effects will be greater.

The feedback path problem has been recognized in the past and several solutions have been proposed with limited success. A first set of proposed solutions has focused on the use, type, and placement of the reference sensors and the secondary sources, while a second set of proposed solutions has focused on signal processing techniques. The first set of proposed solutions involves the use and placement of directional reference sensors and secondary sources to limit or minimize the feedback signal. These proposed solutions add additional expense and complexity to the system and decrease overall reliability while making it difficult, if not impossible, to obtain good directivity over a broad range of frequencies.

The second set of proposed solutions has focused on signal processing techniques and has achieved limited success. The proposed solutions involving signal processing techniques may be generally separated into off-line modeling techniques and on-line modeling techniques. Both off-line modeling and on-line modeling are system identification techniques in which a signal is provided to the system and the resulting signal is analyzed to construct a model of the unknown system. This is accomplished by exciting an unknown path or environment with the known signal and then measuring or analyzing the resulting signal that is provided in response.

Off-line feedback path modeling techniques involve providing a known signal in the absence of the noise signal cancellation that is normally provided by the active noise control system. An adaptive algorithm is used to calculate the coefficients or taps of an adaptive filter to minimize the effects of the feedback path. Once the coefficients or taps are established off-line, during actual active noise control system operation, the taps or coefficients are fixed in a digital filter and are not changed during actual operation. Although off-line feedback path modeling techniques are adequate in certain situations, off-line modeling may not provide adequate performance when used in a system in which parameters are frequently changing. For example, parameters such as temperature and signal flow rate may frequently change resulting in an inaccurate feedback path model because of the changes.

Another problem with off-line feedback path modeling is that the noise signal must be eliminated or stopped for the off-line feedback path modeling to correctly model the unknown environment. This is often not practical in many real-world systems. For example, a power transformer that is energized and used to provide power to customers cannot be easily taken out of service so that off-line modeling may take place. In a system that changes frequently, it may be necessary to routinely perform off-line feedback path modeling so that the feedback path remains accurately modeled. In the event that a noise source cannot be shut off, off-line modeling may proceed if the known signal or modeling signal is provided at a very high amplitude for an extended period of time. In spite of this, the off-line model may still be inaccurate.

On-line feedback path modeling refers to the modeling of the feedback path while the noise signal is being provided to the unknown environment and the active noise control system is operating to cancel the noise signal. Ideally, on-line feedback modeling allows for any changes in the plant environment to be modeled while the active noise control system is operating and thus avoiding the problems encountered with off-line feedback path modeling when the environment or plant changes due to such things as temperature and flow changes. Unfortunately, prior attempts at providing on-line feedback path modeling have proven unsatisfactory and have failed to provide an on-line model of the feedback path.

One such technique focused on providing an adaptive neutralization filter in parallel with the feedback path. The adaptive neutralization filter approach, such as that described in U.S. Pat. No. 4,473,906 entitled “Active Acoustic Attenuator,” may only effectively operate in an off-line feedback path modeling mode because of the fact that the adaptive neutralization filter will attempt to adapt even when the noise signal and the anti-noise signal are perfectly canceled. The feedback neutralization technique attempts to model the feedback path in such a way as to remove all portions of the primary signal that are correlated with the output of the adaptive filter, which, ideally, results in a system that appears to be without feedback. Since the primary noise signal is highly correlated with the anti-noise signal, the adaptive feedback neutralization filter will continue adapt even when the feedback signal is perfectly canceled. As a consequence, the adaptation of the feedback neutralization filter must be deactivated when the system is on-line. Also, when the noise signal contains narrowband frequency components, the adaptive feedback neutralization filter may fail to properly converge when attempting to adapt on-line.

Another proposed on-line feedback path modeling solution involves the use of an infinite-impulse response ("IIR") filter to compensate for the feedback signal. This approach has achieved only limited success. For example, in U.S. Pat. No. 4,677,677 entitled "Active Sound Attenuation System with On-Line Adaptive Feedback Cancellation," an adaptive IIR filter structure was proposed for use in an active noise control system. In this approach, the feedback path is considered part of the overall plant model but does not truly model the feedback path. This approach suffers several disadvantages which are inherent in adaptive IIR filters. For example, IIR filters are not unconditionally stable because of the possibility that some poles of the IIR filter will move outside of the unit circle during the adaptive process, resulting in instability. Also, due to the presence of local minima the adaptation may converge at one of the local minima. Furthermore, adaptive algorithms used with IIR filters often have a relatively slow convergence rate in comparison with that of FIR filters.

Other proposed on-line feedback path modeling solutions involve the use of a modeling signal that must be provided at a very high amplitude so that it may be distinguished from the noise signal. This solution introduce additional noise into the system that adversely affects overall active noise control system operation and performance.

SUMMARY OF THE INVENTION

From the foregoing it may be appreciated that a need has arisen for an active noise control system and method for on-line feedback path modeling that eliminate or reduce the problems described above. In accordance with the present invention, an active noise control system and method for on-line feedback path modeling are provided that provide a signal processing solution to the feedback signal problem by providing on-line modeling of the feedback path and neutralizing its effects so that an active noise control system will operate more efficiently and accurately. This is accomplished even when the feedback path is changing. The present invention attenuates both broadband noise signals and narrowband noise signals.

According to an embodiment of the present invention, an active noise control system is provided for generating an anti-noise signal to attenuate a noise signal provided through a media of a primary path. The active noise control system performs on-line feedback path modeling and feedback path neutralization. The active noise control system includes a reference sensor, a secondary source, an error sensor, and an active noise control system controller. The reference sensor receives the noise signal and a feedback signal and generates a primary signal in response. The secondary source receives a secondary signal and generates a corresponding anti-noise signal in response. The anti-noise signal is provided to the media to attenuate the noise signal. The error sensor receives a residual signal that is a combination of the noise signal and the anti-noise signal as received at the error sensor. The error sensor generates an error signal in response to receiving the residual signal. The active noise control system controller receives the primary signal and the error signal and generates the secondary signal while performing on-line feedback path modeling.

The present invention provides various technical advantages. A technical advantage of the present invention includes the ability to accurately perform on-line feedback path modeling to improve overall active noise control system performance. Another technical advantage of the present invention includes the ability to implement the present invention using existing digital signal processing techniques and algorithms. Yet another technical advantage of the present invention includes increased active noise control system stability due to the elimination of the feedback path effects. Still another technical advantage of the present invention includes the ability to cancel or attenuate both broadband and narrowband noise signals. Other technical advantages are readily apparent to one skilled in the art from the following FIGUREs, description, and claims.

BRIEF DESCRIPTION OF THE DRAWINGS

For a more complete understanding of the present invention and the advantages thereof, reference is now made to the following brief description, taken in connection with the accompanying drawings and detailed description, wherein like reference numerals represent like parts, in which.

DETAILED DESCRIPTION OF THE INVENTION

Figure 1:
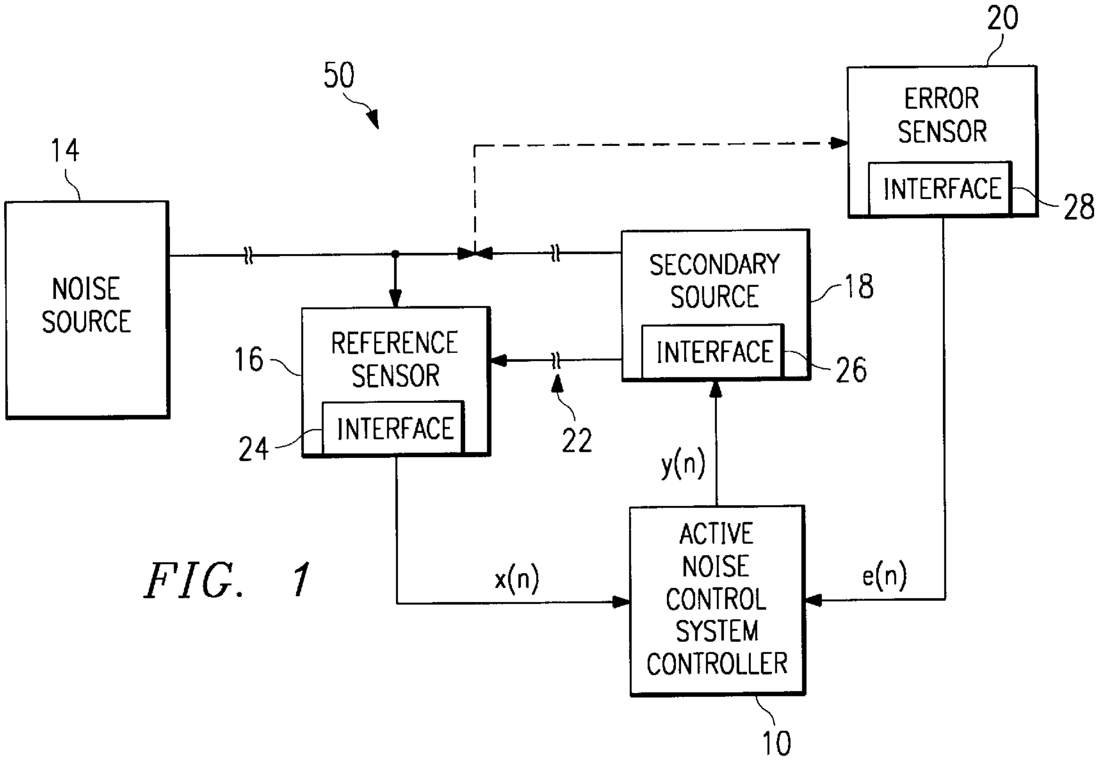
FIG. 1 is a block diagram illustrating a feedforward active noise control system according to the teachings of the present invention.

FIG. 1 is a block diagram of a feedforward active noise control system 50. Feedforward active noise control system 50 includes a noise source 14, a reference sensor 16, an active noise control system controller 10, a secondary source 18, and an error sensor 20. Noise source 14 generates or provides a noise signal through a plant environment where the signal may be received by reference sensor 16. The noise signal is shown flowing from noise source 14 in FIG. 1.

Reference sensor 16 generates a corresponding electronic signal x(n) which may be referred to as a primary signal x(n). Reference sensor 16 may be implemented using virtually any type of sensor such as a microphone, a tachometer, and an accelerometer, to name a few. Reference sensor 16 may also contain an interface circuitry 24 so that the noise signal may be received as an analog signal and the corresponding primary signal x(n) may be generated as a digital signal. Interface circuitry 24 may include any of a variety of devices such as an analog-to-digital converter, an analog filter, an amplifier controlled by an automatic gain control circuit, and any of a variety of other circuitry such as antialiasing circuitry.

Active noise control system controller 10 receives the primary signal x(n) and generates a corresponding electrical signal y(n), which may be referred to as a secondary signal y(n). The secondary signal y(n) is provided to secondary source 18 where it is received and provided back to the plant environment as an analog signal. The output signal of secondary source 18 may be referred to as an anti-noise signal and is designed to reduce, cancel, or neutralize the noise signal provided by noise source 14. Secondary source 18 may be implemented using virtually any signal source such as a speaker, a shaker, or virtually any other available signal source. Secondary source 18 may also include an interface circuitry 26 that allows the secondary signal y(n) to be converted from the digital domain to the analog domain and to be provided at a desired amplitude. Interface circuitry 26 may, for example, include any of variety of circuitry such as a digital-to-analog converter, analog filters, such as a low pass filter, and an amplifier controlled by an automatic gain control circuit.

As a consequence of introducing the anti-noise signal into the plant environment, a portion of the anti-noise signal also travels back to reference sensor 16 along a feedback path that is defined as the path from the output of active noise control system controller 10 to the output of reference sensor 16. A feedback signal 22 is shown flowing through the feedback path and includes, as one of its components, the portion of the anti-noise signal that is provided along the feedback path an may be referred to as an anti-noise feedback component. Feedback signal 22 also includes a modified modeling feedback component that is provided as part of the present invention. The modified modeling feedback component of feedback signal 22 is generated as a result of a modeling signal, that is provided as part of secondary signal y(n) and is discussed more fully below, flowing through the feedback path. Thus, feedback signal 22 includes an anti-noise feedback component and a modified modeling feedback component. Reference sensor 16 receives feedback signal 22 along with the noise signal and generates the primary signal x(n) as a result. Primary signal x(n) will then include a noise signal component and a feedback signal component with the feedback signal component including an anti-noise feedback component and a modified modeling feedback component. The introduction of feedback signal 22 to the input of reference sensor 16 results in the generation of an incorrect primary signal x(n). This will be discussed more fully below.

Error sensor 20 receives a residual signal that is the result of the combination of the noise signal and the anti-noise signal at an acoustical summing junction. The residual signal is ideally zero. The residual signal is zero when the anti-noise signal is provided at the acoustical summing junction at an amplitude equivalent to the noise signal but 180 degrees out of phase with the noise signal and entirely cancels the noise signal at the acoustical summing junction.

Figure 2:
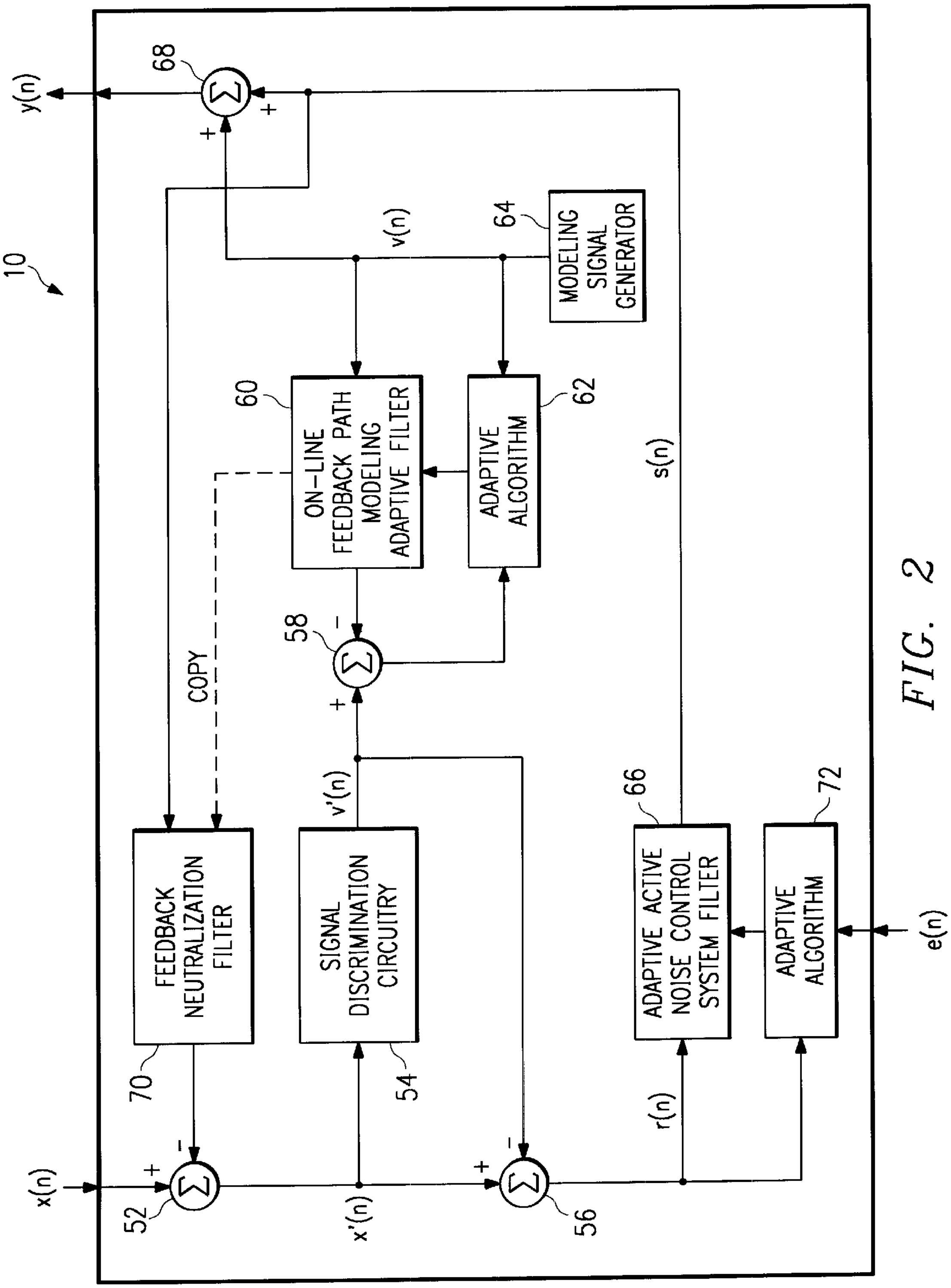
FIG. 2 is a block diagram illustrating an active noise control system controller of the feedforward active noise control system.

Error sensor 20 receives the residual signal and generates a corresponding error signal e(n). E r r o r sensor 20 may be implemented using virtually any sensor. For example, error sensor 20, just as with reference sensor 16, may be implemented using a microphone, a tachometer, an accelerometer, or virtually any other available sensor. Error signal e(n) may be provided in the digital domain through the use of an interface circuitry 28. Interface circuitry 28 may be similar to interface circuitry 24 and may include such circuitry as an analog-to-digital converter, a smoothing filter, and an amplifier controlled by an automatic gain control circuit. Error signal e(n) is provided to active noise control system controller 10 where it is received and used by an adaptive active noise control system filter 66 to provide active noise control so that the generation of the secondary signal y(n) may be adjusted to improve the overall performance of feedforward active noise control system 50. Adaptive active noise control system filter 66 is the main filter of active noise control system controller 10 and is illustrated in FIG. 2 and described more fully below. Active noise control system controller 10 also performs on-line feedback path modeling and feedback path neutralization to reduce the effects of feedback signal 22.

Interface circuitry 24, interface circuitry 26, and interface circuitry 28 are illustrated in FIG. 1 as being provided as part of their respective sensor or source. However, it should be understood that the interface circuitry may be provided as discrete circuitry components provided independently or separately. The present invention is in no way limited by any one particular type of interface circuitry.

Figure 3:
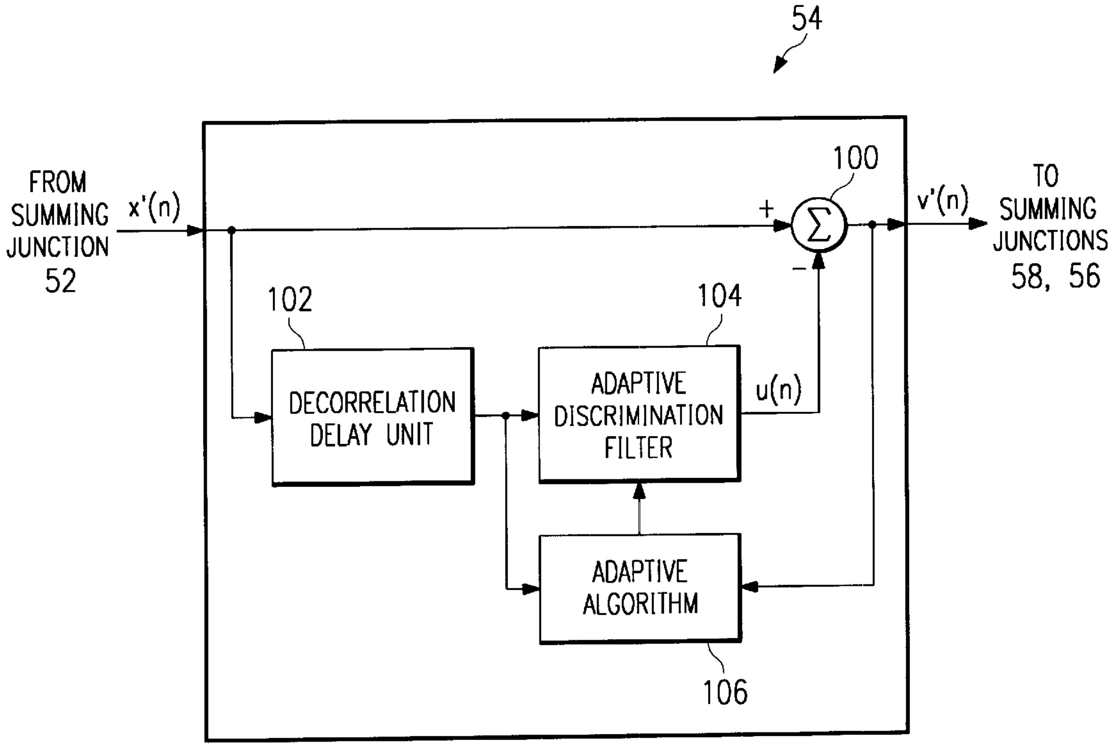
FIG. 3 is a block diagram illustrating a signal discrimination circuitry of the active noise control system controller according to the teachings of the present invention.

Active noise control system controller 10, illustrated more fully in FIGS. 2 and 3, receives primary signal x(n) and error signal e(n) and generates secondary signal y(n) in response. Active noise control system controller 10 includes on-line feedback path modeling circuitry and feedback signal neutralization circuitry. The feedback path may be modeled by a transfer function denoted by F(z). Active noise control system controller 10 also includes an adaptive active noise control system filter 66, which serves as the mean filter, for adaptively modeling the primary plant or environment which has a transfer function denoted by P(z).

Active noise control system controller 10 also includes a modeling signal generator 64 that is used to introduce a modeling signal into feedforward active noise control system so that a feedback excitation signal or modified modeling signal may be generated as a result of the modeling signal having passed through the feedback path. The modified modeling signal becomes correlated to the feedback path as a result of passing through the feedback path. The modified modeling signal is provided as the modified modeling feedback component of feedback signal 22 along with the anti-noise feedback component of feedback signal 22. The modeling signal is normally provided at an amplitude that is significantly smaller than the primary signal x(n) and secondary signal y(n). The modified modeling signal is used in conjunction with the on-line feedback path modeling circuitry and feedback signal neutralization circuitry to provide on-line modeling and feedback signal neutralization. The modeling signal and the modified modeling signal that serves as the modified modeling feedback component of feedback signal 22 are described more fully below in connection with FIGS. 2 and 3. Active noise control system controller 10 controls feedforward active noise control system 50 by reducing or minimizing the error signal e(n) while also performing on-line feedback path modeling of the feedback path which enhances overall system performance and noise canceling capability.

Active noise control system controller 10 may be implemented using digital circuitry such as a digital signal processor. For example, Texas Instruments Incorporated provides a family of digital signal processors including the TMS320C25 and the TMS320C30 digital signal processors. The advent of high-speed digital signal processors and related hardware have made the implementation of the present invention more practical. Many digital signal processors are implemented using a fixed-point data format. In such a case, automatic gain control circuitry must be used at each data input to extend the analog-to-digital converter dynamic range of interface circuitry 24 and interface circuitry 28.

FIG. 2 is a block diagram of active noise control system controller 10. Active noise control system controller 10 receives primary signal x(n) from reference sensor 16 and the error signal e(n) from error sensor 20 and performs various filtering, processing, and modeling functions to generate secondary signal y(n) which is provided to secondary source 18. Primary signal x(n) is received at a summing junction 52 along with the output signal of a feedback neutralization filter 70. Summing junction 52 subtracts the output signal of feedback neutralization filter 70 from primary signal x(n) to generate an output signal x'(n) in response. The signal x'(n) may be referred to as a feedback neutralized primary signal since the anti-noise feedback component of feedback signal 22, which is provided as a component of primary signal x(n), is removed by feedback neutralization filter 70.

Signal discrimination circuitry 54 receives the feedback neutralized primary signal x'(n) and generates an output signal v'(n) which may be referred to as a modified modeling signal because the noise signal component has been removed from feedback neutralized primary signal x'(n) Modified modeling signal v'(n) represents a modeling signal v(n) after having passed through the feedback path. The feedback path, once again, is defined as the plant environment from the output of active noise control system controller 10 to the output of reference sensor 16. Signal discrimination circuitry 54, in effect, extracts the modified modeling feedback component of feedback signal 22 that is included as a component of feedback neutralized primary signal x'(n). This is accomplished in spite of the fact that the magnitude of modeling signal v(n) will generally be significantly less than the magnitude of the noise signal. Signal discrimination circuitry 54 uses a decorrelation delay unit and a digital adaptive filter to generate a predicted noise u(n) signal that does not include any component of feedback signal 22. Predicted noise signal u(n) may then be subtracted from feedback neutralization primary signal x'(n) to generate the modified modeling signal v'(n). Signal discrimination circuitry 54 is illustrated more fully in FIG. 3 and is described in more detail below.

Feedback neutralized primary signal x'(n) is also provided to a summing junction 56 along with modified modeling signal v'(n). Summing junction 56 subtracts modified modeling signal v'(n) from feedback neutralized primary signal x'(n) to generate an output signal r(n) which may be referred to as a processed primary signal. Processed primary signal r(n) will contain the noise signal component of primary signal x(n) after the modified modeling feedback component of feedback signal 22 has been removed from feedback neutralized primary signal x'(n). Processed primary signal r(n) is then provided to the main adaptive filter of feedforward active noise control system 50 which includes adaptive noise control system filter 66 and associated adaptive algorithm 72.

Adaptive active noise control system filter 66 and adaptive algorithm 72 function together to generate an output signal s(n) which may be referred to as a generated secondary signal. Adaptive active noise control system filter 66 receives processed primary signal r(n) while adaptive algorithm 72 receives processed primary signal r(n) and error signal e(n). Adaptive algorithm 72 generates coefficients or taps that may be used by adaptive active noise control system filter 66 to generate output signal s(n) at an appropriate value to cancel the noise signal. Adaptive algorithm 72 generates the taps or coefficients that will minimize the value of error signal e(n). Adaptive active noise control system filter 66 may be implemented as any type of digital adaptive filter, such as an FIR filter or transversal filter, an IIR filter, a lattice filter, a subband filter, or virtually any other digital filter capable of performing adaptive filtering. Preferably, adaptive active noise control system filter 66 will be implemented as an FIR filter for increased stability and performance. The adaptive algorithm used in adaptive algorithm 72 may include any known or available adaptive algorithms such as, for example, a least mean-square (LMS) algorithm, a normalized LMS algorithm, a correlation LMS algorithm, a leaky LMS algorithm, a partial-update LMS algorithm, a variable-step-size LMS algorithm, a signed LMS algorithm, or a complex LMS algorithm. Adaptive algorithm 72 may use a recursive or a non-recursive algorithm depending on how adaptive active noise control system filter 66 is implemented. For example, if adaptive active noise control system filter 66 is implemented as an IIR filter, a recursive LMS algorithm may be used in adaptive algorithm 72. A good overview of the primary adaptive algorithms is provided in Sen M. Kuo & Dennis R. Morgan, *Active Noise Control Systems: Algorithms and DSP Implementations*, (1996).

Modeling signal generator 64 is also provided to generate a modeling signal v(n) which may be provided as a white noise signal or a random signal. Modeling signal generator 64 may use any technique to generate a white noise signal, random signal, or chirp signal, but will generally use one of two basic techniques that can be used for random number or chirp signal generation. The first technique uses a lookup table method using a set of stored samples. The second technique uses a signal generation algorithm. Both techniques obtain a sequence that repeats itself after a finite period, and therefore is not truly random for all time. The modeling signal v(n) may be any signal capable of modeling an environment or path.

Modeling signal v(n) is provided to a summing junction 68 along with generated secondary signal s(n). Modeling signal v(n) is generally provided at an amplitude that is much smaller than either the noise signal or anti-noise signal to reduce its effects on feedforward active noise control system 50. Summing junction 68 sums these two signals and generates the secondary signal y(n) as its output. Thus, secondary signal y(n) will include two components: (1) modeling signal v(n); and (2) generated secondary signal s(n).

An on-line feedback path modeling adaptive filter 60 and a corresponding adaptive algorithm 62 are also provided as part of active noise control system controller 10. On-line feedback path modeling adaptive filter 60 and adaptive algorithm 62 are used to model the feedback path and periodically provide filter coefficient or tap settings to feedback neutralization filter 70. The feedback path, once again, being defined as the plant environment from the output of the active noise control system controller 10 to the output of reference sensor 16. On-line feedback path modeling adaptive filter 60 provides filter tap settings to feedback neutralization filter 70 every fixed number of sample periods. The fixed number of sample periods may be a programmable value and may occur every sample period or, preferably, at every fixed number of sample periods to provide acceptable overall system performance. For example, the fixed number of sample periods may occur every 20 sample periods and will generally be dependent on how frequently the feedback path changes. The sample period is inversely related to the sampling rate, which must be high enough to satisfy the Nyquist criterion such that the sampling rate must be greater than or equal to two times the highest frequency of interest. Also, the real-time digital signal processing performed by active noise control system controller 10, which includes on-line feedback path modeling adaptive filter 60, must be performed at a sample period that is less than the sampling period of feedforward active noise control system 50.

On-line feedback path modeling adaptive filter 60 and adaptive algorithm 62 receive modeling signal v(n) as an input. Adaptive algorithm 62 also receives the output signal of a summing junction 58 as an input which is equivalent to the difference between modified modeling signal v'(n) and the output signal of on-line feedback path modeling adaptive filter 60. The function of adaptive algorithm 62 is to adjust the taps or coefficients of on-line feedback path modeling adaptive filter 60 to minimize the mean-square value of the output signal provided by summing junction 58. The output signal of summing junction 58 may be thought of as an error signal, such as a modeling error signal, to be minimized. Therefore, the filter coefficient or taps are updated so that the error signal is progressively minimized on a sample-bysample basis. On-line feedback path modeling adaptive filter 60 and adaptive algorithm 62 may be implemented as any digital adaptive filter such as those described above with reference to adaptive noise control system filter 66 and adaptive algorithm 72. On-line feedback path modeling adaptive filter 60 and adaptive algorithm 62 provide an on-line feedback path model.

Feedback neutralization filter 70 is a non-adaptive digital filter and receives the tap or coefficient settings from on-line feedback path modeling adaptive filter 60. As mentioned above, these coefficients may be copied from on-line feedback path modeling adaptive filters 60 to feedback neutralization filter 70 every sample period or preferably, at selected intervals. Feedback neutralization filter 70 receives the tap or coefficient information and processes its input signal, generated secondary signal s(n), in response. Feedback neutralization filter 70 filters this signal to generate an output signal that is about equivalent to the anti-noise feedback component of feedback signal 22, which is provided through the feedback path. The output signal of feedback neutralization filter 70 is then provided to summing junction 52 where the anti-noise feedback component of feedback signal 22 is removed from primary signal x(n).

In operation, active noise control system controller 10 receives primary signal x(n) from reference sensor 16 along with error signal e(n) from error sensor 20 as input signals. Primary signal x(n) may be thought of as containing a noise signal component and a feedback signal 22 component. Once again, feedback signal 22 component includes at least two components, the anti-noise feedback component, and the modified modeling feedback component. The primary signal x(n) passes through summing junction 52 where the anti-noise feedback component of feedback signal 22 is removed by feedback neutralized filter 70 to generate feedback neutralized primary signal x'(n). Feedback neutralized primary signal x'(n) is provided to signal discrimination circuitry 54 and summing junction 56.

Signal discrimination circuitry 54 generates modified modeling signal v'(n) in response. Modified modeling signal v'(n) is also provided as an input to summing junction 56. Summing junction 56 subtracts the modified modeling signal v'(n) from feedback neutralized primary signal x'(n) to remove the modified modeling feedback component of x'(n) and to generate processed primary signal r(n). Processed primary signal r(n) is received at both adaptive active noise control system filter 66 and adaptive algorithm 72. Adaptive algorithm 72 also receives error signal e(n) from error sensor 20. Adaptive active noise control system filter 66 provides generated secondary signal s(n) using adaptive algorithm 72 which adjusts the coefficients or taps of adaptive active noise control system filter 66 to minimize error signal e(n). Ideally, generated secondary signal s(n) is about equal to a signal that is 180° out of phase with the noise signal so that the noise signal will be canceled when combined with generated secondary signal s(n) after it is converted to the analog domain by secondary source 18.

Alternatively, summing junction 56 is not provided and the feedback neutralized primary signal x'(n) is provided directly to adaptive active noise control system filter 66 and adaptive algorithm 72. In such a case, feedback neutralized primary signal x'(n) functions as processed primary signal r(n) except that processed primary signal r(n) will include modified modeling signal v'(n) as a component. This may be accomplished because of the fact that the average amplitude of the modified modeling signal v'(n) will generally be significantly less than that of the noise signal component of primary signal x(n). The noise signal component is also included as a component of feedback neutralized primary signal x'(n).

Meanwhile, modeling signal generator 64 provides modeling signal v(n) to summing junction 68, on-line feedback path modeling adaptive filter 60, and adaptive algorithm 62. Modeling signal v(n) is combined with generated secondary signal s(n) at summing junction 68 to generate secondary signal y(n). Secondary signal y(n) is then provided to secondary source 18 so that a corresponding anti-noise signal may be generated to cancel the noise signal. The amplitude of modeling system v(n) will, preferably, be somewhat smaller than the noise signal. This is to allow the modeling signal to excite the feedback path without unduly or significantly affecting the overall plant environment.

On-line feedback path modeling adaptive filter 60 and adaptive algorithm 62 receive modeling signal v(n) and work together to model the feedback path. In doing this, the appropriate taps or coefficients of feedback neutralization filter 70 are calculated by adaptive algorithm 62 and provided to feedback neutralization filter 70 at selected intervals. As mentioned previously, these may be provided, each sample period or at selected intervals. Feedback neutralization filter 70 is then provided to summing junction 52 where the anti-noise feedback component of feedback signal 22 is removed from primary signal x(n).

Thus, active noise control system controller 10 controls feedforward active noise control system 50 so that an anti-noise signal may be generated by secondary source 18 to cancel or attenuate the noise signal. Active noise control system controller 10 provides on-line feedback path modeling and neutralization circuitry to eliminate any adverse effects caused by the presence of the feedback path to improve the overall performance of feedforward active noise control system 50. Active noise control system controller 10 allows for the cancellation of both narrowband and broadband noise signals.

FIG. 3 is a block diagram of signal discrimination circuitry 54 that includes a decorrelation delay unit 102, an adaptive discrimination filter 104, an adaptive algorithm 106, and a summing junction 100. Decorrelation delay unit 102 and summing junction 100 receive feedback neutralized primary signal x'(n) from summing junction 52.

Decorrelation delay unit 102 is a digital delay that delays feedback neutralized primary signal x'(n) by a selected number of sampling periods. Preferably, decorrelation delay unit 102 provides a delay that is equal to or greater than the delay provided through the feedback path. For example, the time it takes for feedback signal 22 to propagate from the output of active noise control system controller 10 to the output of reference sensor 16 is the delay provided through the feedback path. Although the delay of decorrelation delay unit 102 is preferably set at a delay that is equal to or greater than the delay of the feedback path, performance is enhanced with a delay time as low as one sample period. Thus, the present invention encompasses a delay of one sample period or more.

Adaptive discrimination filter 104 and adaptive algorithm 106 both receive the output signal from decorrelation delay unit 102. Adaptive algorithm 106 also receives modified modeling signal v'(n) as an input signal and uses this as an error signal. Adaptive algorithm 106 calculates the taps or coefficients for adaptive discrimination filter 104 that will minimize the modified modeling signal v'(n). In response, adaptive discrimination filter 104 receives the output of decorrelation delay unit 102 and generates predicted noise signal u(n) which, ideally, is equivalent to the actual noise signal. Thus, the modified modeling feedback component is removed and predicted noise signal u(n) is provided to summing junction 100 where it is subtracted from feedback neutralized primary signal x'(n) to generate modified modeling signal v'(n) by removing the noise signal component of feedback neutralized primary signal x'(n).

Adaptive algorithm 106 may be implemented using any of a variety of known and available adaptive algorithms such as those described previously in connection with adaptive algorithm 72 and adaptive algorithm 62. Adaptive discrimination filter 104 may be any type of digital filters such as an FIR or an IIR filter. Decorrelation delay unit 102 may be implemented using a computer memory or register so that a desired delay in feedback neutralized primary signal x'(n) may be provided to decorrelate the modified modeling feedback component of feedback neutralized primary signal x'(n) while leaving the narrowband components correlated. As a consequence of the delay, adaptive discrimination filter 104 will only be able to predict or generate the signal components that remain correlated.

Thus, it is apparent that there has been provided, in accordance with the present invention, an active noise control system and method for on-line feedback path modeling that eliminate or reduce the adverse effects of the feedback path on overall system operation and that satisfy the advantages set forth above. Although the preferred embodiment has been described in detail, it should be understood that various changes, substitutions, and alterations can be made herein without departing from the scope of the present invention. It should also be understood that the present invention may be implemented to reduce any noise source including, but not limited to, vibrations, acoustical signals, electrical signals, and the like. The circuits and functional blocks described and illustrated in the preferred embodiment as discrete or separate circuits or functional blocks may be combined into one or split into separate circuits or functional blocks without departing from the scope of the present invention. Furthermore, the direct connections illustrated herein could be altered by one skilled in the art such that two circuits or functional blocks are merely coupled to one another through an intermediate circuit or functional block without being directly connected while still achieving the desired results demonstrated by the present invention. Also, the specified signals illustrated herein could be altered by one skilled in the art such that a signal is merely processed or summed with another signal during an intermediate step while still achieving the desired results demonstrated by the present invention. For example, the feedback neutralized primary signal may be provided to adaptive active noise control system filter 66 with or without having the modified modeling signal v'(n) subtracted. Other examples of changes, substitutions, and alterations are readily ascertainable by one skilled in the art and could be made without departing from the spirit and scope of the present invention as defined by the following claims.

What is claimed is:

1. An active noise control system for generating an anti-noise signal to attenuate a noise signal provided through a media, the active noise control system performing on-line feedback path modeling and feedback path neutralization, the active noise control system comprising:

- a reference sensor operable to receive the noise signal and a feedback signal and to generate a primary signal in response;
- a secondary source operable to receive a secondary signal and to generate a corresponding anti-noise signal that is provided to the media to attenuate the noise signal;
- an error sensor operable to receive a residual signal that is the combination of the noise signal and the anti-noise signal as received at the error sensor, and to generate an error signal in response; and
- an active noise control system controller operable to receive the primary signal and the error signal and to generate the secondary signal while performing on-line feedback path modeling, the active noise control system controller including:
  - a first summing junction operable to subtract an anti-noise feedback component from the primary signal to generate a feedback neutralized primary signal;
  - a system adaptive filter operable to receive the feedback neutralized primary signal and the error signal and to filter the feedback neutralized primary signal to generate a generated secondary signal;
  - a modeling signal generator operable to generate a modeling signal; and
  - a second summing junction operable to combine the generated secondary signal with the modeling signal to generate the secondary signal.

2. The active noise control system of claim 1, wherein the active noise control system controller further includes:

- an on-line feedback path modeling adaptive filter operable to receive the modeling signal and a modeling error signal and to filter the modeling signal to generate an output signal;
- a signal discrimination circuitry operable to receive the feedback neutralized primary signal and to generate a modified modeling signal;
- a third summing junction operable to subtract the output signal from the modified modeling signal to generate the modeling error signal which is provided to an adaptive algorithm used by the on-line feedback path modeling adaptive filter; and
- a feedback neutralization filter operable to receive the generated secondary signal and to generate a signal containing the anti-noise feedback component that is provided to the first summing junction, and wherein the adaptive algorithm used by the on-line feedback path modeling adaptive filter is operable to calculate filter taps of the on-line feedback path modeling adaptive filter to minimize the mean-square value of the modeling error signal, and the filter taps are provided to the feedback neutralization filter and used by the feedback neutralization filter to generate the signal containing the anti-noise feedback component.

3. The active noise control system of claim 2, further comprising:

- a fourth summing junction operable to subtract the modified modeling signal from the feedback neutralized primary signal to generate a processed primary signal, and wherein the system adaptive filter is operable to receive the processed primary signal and the error signal and to filter the processed primary signal to generate the generated secondary signal.

4. The active noise control system of claim 1, further comprising:

- a first interface circuit operable to convert the primary signal from the analog domain to the digital domain and to provide the primary signal to the active noise control system controller in the digital domain;
- a second interface circuit operable to convert the secondary signal from the digital domain to the analog domain and to provide the secondary signal to the secondary source in the analog domain; and
- a third interface circuit operable to convert the error signal from the analog domain to the digital domain and to provide the error signal to the active noise control system controller in the digital domain.

5. The active noise control system of claim 4, wherein the reference sensor includes the first interface circuit, the secondary source includes the second interface circuit, and the error sensor includes the third interface circuit.

6. The active noise control system of claim 1, wherein the primary signal includes a noise signal component and a feedback signal component.

7. The active noise control system of claim 6, wherein the feedback signal component includes an anti-noise feedback component and a modified modeling feedback component.

8. The active noise control system of claim 7, wherein the secondary signal includes a generated secondary signal component and a modeling signal component.

9. The active noise control system of claim 8, wherein the average amplitude of the modeling signal component of the secondary signal is smaller than the average amplitude of the generated secondary signal component.

10. The active noise control system of claim 1, wherein the active noise control system is a feedforward active noise control system.

11. The active noise control system of claim 1, wherein the active noise control system controller uses digital circuitry.

12. The active noise control system of claim 1, wherein the reference sensor is a microphone, the secondary source is a speaker, and the error sensor is a microphone.

13. An active noise control system controller for receiving a primary signal and an error signal and generating a secondary signal in response, the active noise control system controller performing on-line feedback path modeling and feedback path neutralization, the active noise control system controller comprising:

a first summing junction operable to subtract an anti-noise feedback component from the primary signal to generate a feedback neutralized primary signal;

a system adaptive filter operable to receive the feedback neutralized primary signal and the error signal and to filter the feedback neutralized primary signal to generate a generated secondary signal;

a modeling signal generator operable to generate a modeling signal; and a second summing junction operable to combine the generated secondary signal with the modeling signal to generate the secondary signal.

14. The active noise control system controller of claim 13, further comprising:

an on-line feedback path modeling adaptive filter operable to receive the modeling signal and a modeling error signal and to filter the modeling signal to generate an output signal;

a signal discrimination circuitry operable to receive the feedback neutralized primary signal and to generate a modified modeling signal; and a third summing junction operable to subtract the output signal from the modified modeling signal to generate the modeling error signal which is provided to an adaptive algorithm used by the on-line feedback path modeling adaptive filter.

15. The active noise control system controller of claim 14, further comprising:

a fourth summing junction operable to subtract the modified modeling signal from the feedback neutralized primary signal to generate a processed primary signal, and wherein the system adaptive filter is operable to receive the processed primary signal and the error signal and to filter the processed primary signal to generate the generated secondary signal.

16. The active noise control system controller of claim 14, further comprising:

a feedback neutralization filter operable to receive the generated secondary signal and to generate a signal containing the anti-noise feedback component that is provided to the first summing junction.

17. The active noise control system controller of claim 16, wherein the adaptive algorithm used by the on-line feedback path modeling adaptive filter is operable to calculate filter taps of the on-line feedback path modeling adaptive filter to minimize the mean-square value of the modeling error signal.

18. The active noise control system controller of claim 17, wherein the filter taps are provided to the feedback neutralization filter and used by the feedback neutralization filter to generate the signal containing the anti-noise feedback component.

19. The active noise control system controller of claim 18, wherein the filter taps are provided to the feedback neutralization filter at desired intervals.

20. The active noise control system controller of claim 14, wherein the signal discrimination circuitry includes:

a decorrelation delay unit operable to delay the feedback neutralized primary signal and to provide a delayed feedback neutralized primary signal;

an adaptive discrimination filter operable to receive the delayed feedback neutralized primary signal and the modified modeling signal and to filter the delayed feedback neutralized primary signal to generate a predicted noise signal; and a fourth summing junction operable to subtract the predicted noise signal from the feedback neutralized primary signal to generate the modified modeling signal.

21. The active noise control system controller of claim 20, wherein the decorrelation delay unit is implemented using digital circuity.

22. The active noise control system controller of claim 21, wherein the delay of the decorrelation delay unit is a programmable delay.

23. The active noise control system controller of claim 20, wherein the delay is equal to or greater than the delay of the feedback path being modeled.

24. The active noise control system controller of claim 23, wherein the feedback path is defined as the environment from the output of the active noise control system controller to the output of a reference sensor.

25. The active noise control system controller of claim 13, wherein the active noise control system controller is implemented using digital circuitry.

26. The active noise control system controller of claim 13, wherein the modeling signal generator is a white noise generator.

27. The active noise control system controller of claim 13, wherein the modeling signal generator is a random noise generator.

28. The active noise control system controller of claim 13, wherein the modeling signal is a linear chirp signal.

29. The active noise control system controller of claim 13, wherein an adaptive algorithm of the system adaptive filter is a least-means-square adaptive algorithm.

30. The active noise control system controller of claim 13, further comprising:

an on-line feedback path modeling adaptive filter operable to receive the modeling signal and a modeling error signal and to filter the modeling signal to generate an output signal;

a signal discrimination circuitry operable to receive the feedback neutralized primary signal and to generate a modified modeling signal;

a third summing junction operable to subtract the output signal from the modified modeling signal to generate the modeling error signal which is provided to an adaptive algorithm used by the on-line feedback path modeling adaptive filter;

a feedback neutralization filter operable to receive the generated secondary signal and to generate a signal containing the anti-noise feedback component that is provided to the first summing junction, wherein the adaptive algorithm used by the on-line feedback path modeling adaptive filter is operable to calculate filter taps of the on-line feedback path modeling adaptive filter to minimize the mean-square value of the modeling error signal, and wherein the filter taps are provided to the feedback neutralization filter and used by the feedback neutralization filter to generate the signal containing the anti-noise feedback component; and wherein the signal discrimination circuitry includes:

a decorrelation delay unit operable to delay the feedback neutralized primary signal and to provide a delayed feedback neutralized primary signal, an adaptive discrimination filter operable to receive the delayed feedback neutralized primary signal and the modified modeling signal and to filter the delayed feedback neutralized primary signal to generate a predicted noise signal, and a fourth summing junction operable to subtract the predicted noise signal from the feedback neutralized primary signal to generate the modified modeling signal.

31. A method for on-line feedback path modeling comprising the steps of:

receiving a primary signal;

generating a modeling signal;

generating filter taps for use in a feedback neutralization filter using the modeling signal and a modified modeling signal;

generating a feedback neutralized primary signal using the feedback neutralization filter and the primary signal;

generating the modified modeling signal using the feedback neutralized primary signal;

receiving an error signal;

generating a generated secondary signal using the feedback neutralized primary signal and the error signal; and generating a secondary signal using the generated secondary signal and the modeling signal.

32. The method of claim 31, wherein the generating the modified modeling signal step includes using a digital delay that is equal to or greater than the delay of the feedback path being modeled.

33. The method of claim 31, wherein the feedback neutralization filter filters the generated secondary signal using the generated filter taps to generate an anti-noise feedback component which may be subtracted from the primary signal to generate the feedback neutralized primary signal.

* * * * *